United States Patent
Gerke et al.

(10) Patent No.: US 9,593,063 B2
(45) Date of Patent: Mar. 14, 2017

(54) PHOTOLABILE PRO-FRAGRANCES

(71) Applicant: Henkel AG & Co. KGaA, Duesseldorf (DE)

(72) Inventors: Thomas Gerke, Duesseldorf (DE); Christian Kropf, Hilden (DE); Ursula Huchel, Cologne (DE); Axel Griesbeck, Cologne (DE); Bjoern Porschen, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/949,162

(22) Filed: Nov. 23, 2015

(65) Prior Publication Data

US 2016/0075628 A1    Mar. 17, 2016

Related U.S. Application Data

(63) Continuation of application No. PCT/EP2014/060331, filed on May 20, 2014.

(30) Foreign Application Priority Data

May 29, 2013 (DE) .................. 10 2013 209 988

(51) Int. Cl.
*C07C 45/45* (2006.01)
*C07C 45/62* (2006.01)
*C07C 49/798* (2006.01)
*C07C 45/44* (2006.01)

(52) U.S. Cl.
CPC ............ *C07C 49/798* (2013.01); *C07C 45/44* (2013.01); *C07C 45/45* (2013.01); *C07C 45/62* (2013.01); *C07C 2101/14* (2013.01)

(58) Field of Classification Search
CPC ........ C07C 45/45; C07C 45/62; C07C 49/798
USPC .............................. 568/329; 512/21; 427/558
See application file for complete search history.

(56) References Cited

U.S. PATENT DOCUMENTS

2010/0137178 A1    6/2010  Smets et al.
2012/0308738 A1   12/2012  Gerke et al.

FOREIGN PATENT DOCUMENTS

WO    2011/101179 A1    8/2011

OTHER PUBLICATIONS

PCT International Search Report (PCT/EP2014/060331) dated Apr. 11, 2014.
Lee et al., "One-Pot Synthesis of a,B-unsaturated Ketones", XP055146870, Synthesis, pp. 213-214, 1991.

*Primary Examiner* — Sikarl Witherspoon
(74) *Attorney, Agent, or Firm* — Thomas G. Krivulka

(57) ABSTRACT

The present invention relates to a method for producing photocleavable scent precursors, to products containing the scent precursors, and to the use of the scent precursors for prolonging the scent impression in the product and on surfaces treated with the product.

8 Claims, No Drawings

PHOTOLABILE PRO-FRAGRANCES

FIELD OF THE INVENTION

The present invention generally relates to a method for preparing pro-fragrances, selected pro-fragrances per se, and products in which such pro-fragrances are used. The invention further relates to the use of pro-fragrances for prolonging the scent impression.

BACKGROUND OF THE INVENTION

Detergents or cleaning agents, cosmetic agents, adhesives or printing inks typically contain scents that impart a pleasant smell to the products. The scents not only mask a potential odor of other ingredients, but also produce a pleasant smell impression in the consumer.

Scents are important components of the composition, in particular in the field of detergents and cleaning agents, since laundry should have a pleasant and substantially fresh smell when damp as well as when dry.

The fundamental problem one faces when using scents in detergents or cleaning agents, cosmetic agents, adhesives or printing inks is that, despite the scents being substantially volatile compounds, it is still desirable to produce a long-lasting scent effect. In particular when using scents that represent fresh and light notes of the perfume and, due to the high vapor pressure thereof, vaporize particularly quickly, the desired long-lasting nature of the scent impression is difficult to achieve.

One option for the delayed release of scents is the use of what are known as photo-activatable substances as pro-fragrances. The action of sunlight or other electromagnetic radiation having a certain wavelength induces the cleavage of a covalent bond in the pro-fragrance molecule, whereby a scent is released.

In this connection, WO 2011/101179 A1 discloses special ketones as photo-activatable substances, which in the presence of sunlight release a scent comprising at least one cyclic double bond in a photochemical fragmentation process.

Starting from the scent, the described pro-fragrances are prepared in a two-stage synthesis by hydroboration of the at least one cyclic double bond and a subsequent substitution reaction.

One disadvantage of the synthesis method described in WO 2011/101179 A1 is that scents, which in addition to the at least one cyclic double bond, also include one or more semicyclic and/or exocyclic double bonds, cannot be selectively reacted, or cannot be reacted at all, to yield the desired pro-fragrances, since the sterically least hindered double bond is the first to react during hydroboration of the scent. One disadvantage of these undesirable constitutional isomers is that they are cleaved only inadequately, or not all, upon irradiation with light and do not release the stored scent.

It was therefore the object of the present invention to provide a simple method for selectively preparing a pro-fragrance that not only ensures effective release of the stored scent, but also stores scents which, in addition to at least one cyclic double bond, can comprise further semicyclic and/or exocyclic double bonds.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method for producing a ketone of general formula (I),

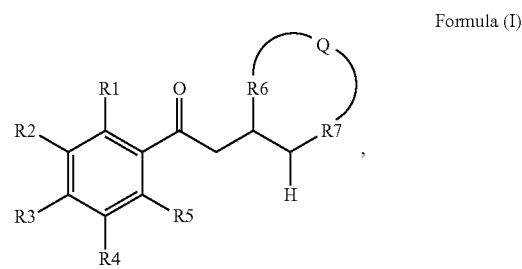

Formula (I)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^|$(alkyl)$_3$, or R1 and R2, or R2 and R3, can denote a bridging substituted or unsubstituted cycloalkyl, cycloalkenyl, aryl or heterocycle residue; and R6 and R7, independently of one another, denote a secondary, tertiary or quaternary C-atom; and Q denotes an R6 and R7 bridging substituted or unsubstituted group having 1 to 10 carbon atoms; characterized in that a) a ketone of general formula (II)

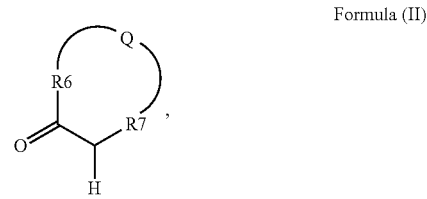

Formula (II)

where the groups R6, R7 and Q are identical to general formula (I), in the presence of a phosphonate of general formula (III),

Formula (III)

where R8 and R9, independently of one another, each denote a linear or branched, substituted or unsubstituted alkoxy group having 1 to 15 carbon atoms, is reacted with a benzonitrile of general formula (IV), A product comprising a ketone of general formula (I),

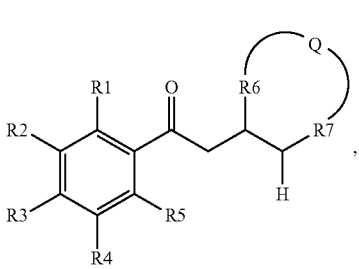

Formula (I)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue; and R6 and R7, independently of one another, denote a secondary, tertiary or quaternary C-atom; and Q denotes an R6 and R7 bridging substituted or unsubstituted group having 1 to 10 carbon atoms; producible by a method, characterized in that a) a ketone of general formula (II)

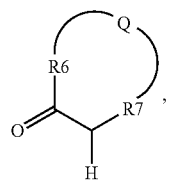

Formula (II)

where the groups R6, R7 and Q are identical to general formula (I), in the presence of a phosphonate of general formula (III),

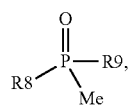

Formula (III)

where R8 and R9, independently of one another, each denote a linear or branched, substituted or unsubstituted alkoxy group having 1 to 15 carbon atoms, is reacted with a benzonitrile of general formula (IV),

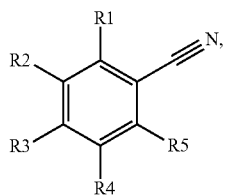

Formula (IV)

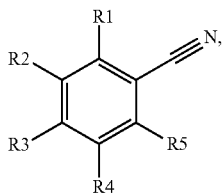

Formula (IV)

where the groups R1, R2, R3, R4 and R5 are identical to general formula (I), and subsequently b) the alpha,beta-unsaturated ketone of general formula (V) obtained in step a),

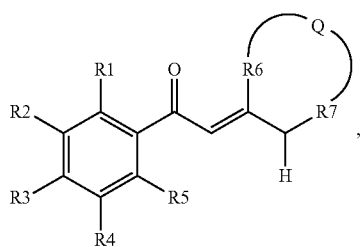

Formula (V)

where the groups R1 to R7 and Q are identical to general formula (I), is selectively hydrogenated to yield a ketone of general formula (I).

A ketone of general formula (VI)

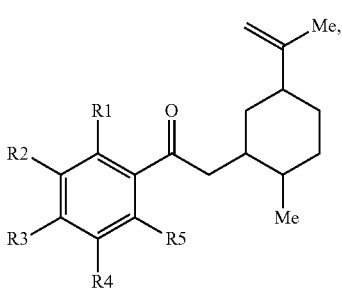

Formula (VI)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue; producible by reacting dihydrocarvone with a benzonitrile of general formula (IV) in the presence of a phosphonate of general formula (III), and subsequently selectively hydrogenating the alpha,beta-unsaturated ketone obtained in step a) to yield a ketone of general formula (VI).

where the groups R1, R2, R3, R4 and R5 are identical to general formula (I), and subsequently b) the alpha,beta-unsaturated ketone of general formula (V) obtained in step a),

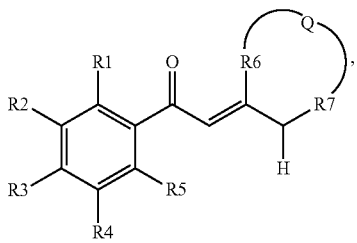

Formula (V)

where the groups R1 to R7 and Q are identical to general formula (I), is selectively hydrogenated to yield a ketone of general formula (I).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The object of the present invention was achieved by a method for producing a ketone of general formula (I),

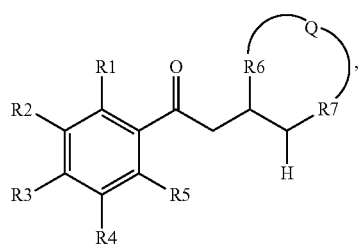

Formula (I)

where R1, R2, R3, R4 and R5, independently of one another, can each denote hydrogen, —$NO_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —$NH_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, and R6 and R7, independently of one another, denote a secondary, tertiary or quaternary C-atom, and Q denotes an R6 and R7 bridging substituted or unsubstituted group having 1 to 10 carbon atoms, in which a) a ketone of general formula (II)

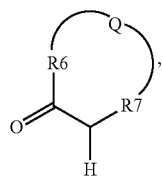

Formula (II)

where the groups R6, R7 and Q are identical to general formula (I), in the presence of a phosphonate of general formula (III),

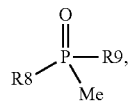

Formula (III)

where R8 and R9, independently of one another, each denote a linear or branched, substituted or unsubstituted alkoxy group having 1 to 15 carbon atoms, is reacted with a benzonitrile of general formula (IV),

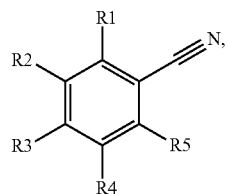

Formula (IV)

where the groups R1, R2, R3, R4 and R5 are identical to general formula (I), and subsequently
b) the alpha,beta-unsaturated ketone of general formula (V) obtained in step a),

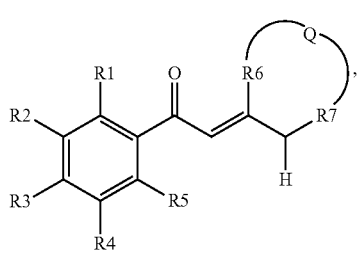

Formula (V)

where the groups R1 to R7 and Q are identical to general formula (I),
is selectively hydrogenated to yield a ketone of general formula (I).

The term "secondary C-atom" within the meaning of the invention shall be understood to mean a carbon atom that is covalently bound to two further carbon atoms. The term "tertiary C-atom" or "quaternary C-atom" within the meaning of the invention shall be understood to mean a C-atom that is covalently bound to three or four further carbon atoms, wherein a tertiary C-atom or a quaternary C-atom within the meaning of the invention can also be a carbon atom that is covalently bound to only two (tertiary) or three (quaternary) further carbon atoms and forms a double bond with one of the two or three carbon atoms.

Surprisingly it was found that the method according to the invention can be used to selectively obtain pro-fragrances of general formula (I) in a simple manner, in which scents comprising at least one cyclic double bond are stored and which effectively again release the stored scent comprising at least one cyclic double bond upon irradiation with light.

The term "scent" within the meaning of the present invention does not refer to the ketone of general formula (II) for synthesis of the pro-fragrance of general formula (I), but to the compound that is released from the pro-fragrance upon exposure to light. This distinguishes the method according to the invention from the method described in WO 2011/101179 A1, where the scent to be released is used as the starting compound.

In a preferred embodiment of the invention, the ketone of general formula (II) comprises at least one semicyclic or exocyclic double bond.

Previously it was not possible to selectively store scents comprising at least one cyclic double bond and at least one semicyclic or exocyclic double bond in pro-fragrances of general formula (I), since the hydroboration step of the method known from the prior art for preparing such pro-fragrances is preferably carried out on the sterically least hindered double bond. The method according to the invention, in contrast, makes it possible to selectively prepare the desired pro-fragrance of general formula (I), regardless of the number of semicyclic or exocyclic double bonds of the released scent.

In a further preferred embodiment of the invention, the bridging portion —CH—R7-Q-R6- of the ketone of general formula (I) is a hydrocarbon.

The scents for the above-described ketone of general formula (II), in which the carbonyl group of the ketone of general formula (II) is a methylene or methine group, are characterized by the high vapor pressure thereof and are difficult to chemically bind to conventional carrier media because they often have a low degree of functionalization. As a result of the method according to the invention, it is now possible to make pro-fragrances available which release these scents in a targeted manner over an extended period.

In a particularly preferred embodiment of the invention, the ketone of general formula (II) is dihydrocarvone.

According to the method according to the invention, a pro-fragrance of general formula (I) that releases limonene upon irradiation with light is obtained from dihydrocarvone, limonene being one of the most important scents in the field of detergents and cleaning agents. The smell of limonene is frequently associated with freshness, which to consumers is synonymous with cleanliness/purity.

In a further preferred embodiment of the invention, the groups R8 and R9 of the phosphonate of general formula (III), independently of one another, each are methoxy, ethoxy, butoxy or isopropoxy residues.

Phosphonates comprising these groups R8 and R9 offer a good compromise between good solubility and stability of the phosphonate, low steric demands, and good reactivity.

In a further preferred embodiment of the invention, the groups R1 to R5, independently of one another, each denote hydrogen, methyl groups or methoxy groups, methoxy groups being particularly preferred.

Nitriles comprising these groups R1 to R5 are either commercially available or synthetically readily accessible and influence the absorption spectrum of the pro-fragrance in an advantageous manner. By appropriately selecting the groups R1 to R5, the release rate of the stored scent upon irradiation with preferably natural sunlight, or commercially available luminous elements, may thus be increased or slowed down.

In still another preferred embodiment of the invention, the hydrogenating agent is selected from the group of alkali metal borohydrides, sodium borohydride being particularly preferred.

Alkali metal borohydrides, and sodium borohydride in particular, are easy to handle due to the solid form of the same, and selectively hydrogenate the semicyclic double bond of the alpha,beta-unsaturated ketone (V).

A further subject matter of the invention is a ketone of general formula (VI),

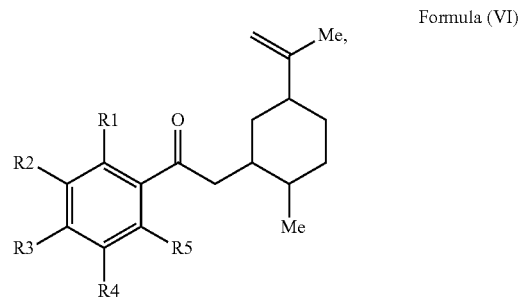

Formula (VI)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, producible by a) reacting dihydrocarvone with a benzonitrile of general formula (IV) in the presence of a phosphonate of general formula (III), and subsequently b) selectively hydrogenating the alpha,beta-unsaturated ketone obtained in step a) to yield a ketone of general formula (VI).

A ketone of general formula (VI) is of particular interest from a perfume-related point of view since the stored scent (limonene) is one of the most important base components of many perfume compositions. Free limonene consists exclusively of carbon and hydrogen, is volatile and, in addition to the cyclic double bond thereof, includes an exocyclic double bond, which is why the targeted storage of limonene using the method according to WO 2011/101179 A1 as a ketone of general formula (VI) was previously not possible.

A further subject matter of the invention is a product comprising a ketone of general formula (I),

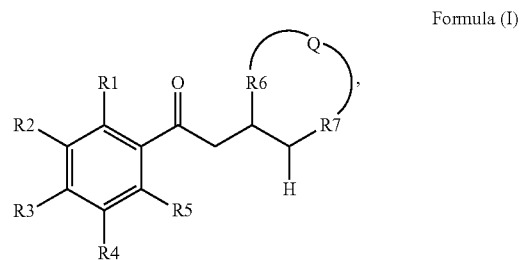

Formula (I)

where R1, R2, R3, R4 and R5, independently of one another, can each denote hydrogen, —NO₂, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH₂, halogen, —NH-alkyl, —N(alkyl)₂ or —N⁺(alkyl)₃, or R1 and R2, or R2 and R3, can denote a bridging substituted or unsubstituted cycloalkyl, cycloalkenyl, aryl or heterocycle residue, and R6 and R7, independently of one another, denote a secondary, tertiary or quaternary C-atom, and Q denotes an R6 and R7 bridging substituted or unsubstituted group having 1 to 10 carbon atoms, producible by a method in which a) a ketone of general formula (II)

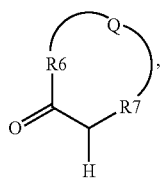

Formula (II)

where the groups R6, R7 and Q are identical to general formula (I), in the presence of a phosphonate of general formula (III),

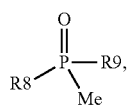

Formula (III)

where R8 and R9, independently of one another, each denote a linear or branched, substituted or unsubstituted alkoxy group having 1 to 15 carbon atoms, is reacted with a benzonitrile of general formula (IV),

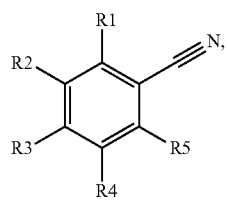

Formula (IV)

where the groups R1, R2, R3, R4 and R5 are identical to general formula (I), and subsequently b) the alpha,beta-unsaturated ketone of general formula (V) obtained in step a),

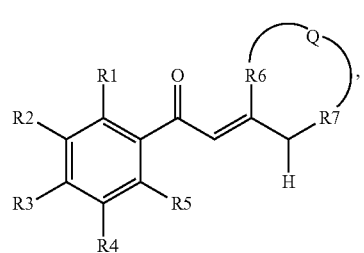

Formula (V)

where the groups R1 to R7 and Q are identical to general formula (I), is selectively hydrogenated to yield a ketone of general formula (I).

A product, comprising a ketone of general formula (I), supplies a pleasant scent impression even after a long storage time, since the scents stored in the pro-fragrances are not released again until irradiated with preferably natural sunlight, or commercially available luminous elements. Premature vaporization of the scent is thereby prevented.

In a preferred embodiment of the invention, the product is a detergent or cleaning agent, a cosmetic agent, an adhesive or a printing ink.

In a further preferred embodiment of the invention, the ketone of general formula (I) used in the product is a ketone of general formula (VI).

Consumers expressly desire a fresh scent impression, in particular in detergents or cleaning agents. A detergent or cleaning agent containing a ketone of general formula (VI) is therefore particularly advantageous since the ketone is a limonene storage compound, and consumers associate the smell of limonene with freshness.

In a further preferred embodiment of the invention, the agent comprises the ketone of general formula (I) in quantities between 0.0001 and 10 wt. %, advantageously between 0.0005 and 5 wt. %, more advantageously between 0.001 and 3 wt. %, in particular between 0.005 and 2 wt. %, the respective percent by weight being based on the total agent.

Since a ketone of general formula (I) has considerably lower vapor pressure than the corresponding scent thereof, lower quantities of the pro-fragrance can be used than of the scent itself to achieve a long-lasting scent effect, which is advantageous from an ecological and economical view.

A further subject matter of the invention is the use of a ketone of general formula (I),

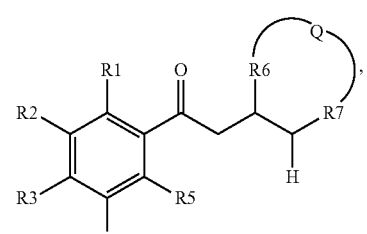

Formula (I)

where R1, R2, R3, R4 and R5, independently of one another, can each denote hydrogen, —NO₂, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, and R6 and R7, independently of one another, denote a secondary, tertiary or quaternary C-atom, and Q denotes an R6 and R7 bridging substituted or unsubstituted group having 1 to 10 carbon atoms, producible by the method according to the invention, in a detergent or cleaning agent, a cosmetic agent, an adhesive or a printing ink for prolonging the scent impression of the detergent or cleaning agent, cosmetic agent, adhesive or of the printing ink.

A further subject matter of the invention is the use of a ketone of general formula (I),

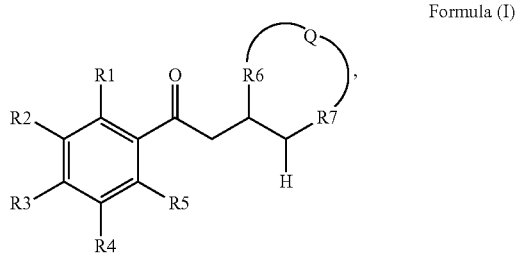

Formula (I)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, and R6 and R7, independently of one another, denote a secondary, tertiary or quaternary C-atom, and Q denotes an R6 and R7 bridging substituted or unsubstituted group having 1 to 10 carbon atoms, producible by the method according to the invention, for prolonging the scent impression on a surface treated with a detergent or cleaning agent, a cosmetic agent, an adhesive or a printing ink.

The invention will be described in greater detail hereafter based on examples, among other things.

The method according to the invention for producing a ketone of general formula (I) relates to a two-stage method, in which initially a ketone of general formula (II) is reacted with a benzonitrile of general formula (IV) in the presence of a phosphonate of general formula (III), and subsequently the resulting alpha,beta-unsaturated ketone of general formula (V) is selectively hydrogenated to yield a ketone of general formula (I).

The reaction of the ketone of general formula (II) with the phosphonate of general formula (III) and the nitrile of general formula (IV) is preferably carried out in a solvent. Suitable solvents are polar aprotic solvents, such as tetrahydrofuran (THF), diethyl ether, acetone, dichloromethane, dimethylformamide (DMF), ethylene glycol dimethyl ether (DM) or mixtures thereof. In particular THF, diethyl ether and DME are particularly preferred solvents within the meaning of the present invention.

The reaction is preferably carried out in the presence of a base. The base used can be a base that is known to a person skilled in the art and is able to deprotonate the phosphonate of general formula (III). Preferably strong bases are used, for example alkali metal hydrides, alkali metal-bis(trimethylsilyl)amides, alkali metal alcoholates or n-butyllithium, the base not being limited to the examples cited here. Within the meaning of the present invention, n-butyllithium is particularly preferred.

The reaction temperature is preferably between −100° C. and 100° C. and is set as a function of the reactivity of the individual reagents. For example, the temperature of the reaction solution may initially be −78° C. and incrementally increased during the course of the reaction, for example to room temperature, which is to say 20 to 25° C.

A nitrile of general formula (IV) is preferred when the groups R1, R2, R3, R4 and R5, independently of one another, each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, denote a bridging substituted or unsubstituted cycloalkyl, cycloalkenyl, aryl or heterocycle residue.

In a further preferred embodiment of the invention, four of the five aryl substituents R1, R2, R3, R4, and R5 denote hydrogen. R1, R2, R4 and R5 preferably denote hydrogen, while the substituent at para position R3 denotes a halogen atom, in particular —F, —Cl, —Br or —I, NO$_2$, a linear or branched, substituted or unsubstituted alkoxy group have 1 to 15 C-atoms, or a linear or branched, substituted or unsubstituted alkyl group having 1 to 15 C-atoms. In a most preferred embodiment of the invention, R3 denotes —Cl, —Br, —NO$_2$ or an alkyl group or alkoxy group comprising 1 to 4 C-atoms. The linear or branched, substituted or unsubstituted alkyl group is preferably a methyl or ethyl group and/or the linear or branched, substituted or unsubstituted alkoxy group is preferably a methoxy, ethoxy, isopropoxy or tert-butoxy group, a methoxy group being most particularly preferred.

A substitution at para position R3 is particularly preferred since the electronic structure of the aromatic ring can be modified most effectively here, whereby the absorption maximum of a ketone of general formula (I) can be easily adapted to a certain wavelength.

A ketone of general formula (I) in which R1, R2, R3, R4 and R5 denote hydrogen is likewise preferred.

The nitrile of general formula (IV) is used in relation to the phosphonate of general formula (III) at a ratio of preferably 1:5 to 5:1, more preferably 1:2 to 2:1, and particularly preferably 1:1.5 to 1.5:1.

A ketone of general formula (II) is preferred when the groups R6 and R7, independently of one another, denote a secondary, tertiary or quaternary C-atom, and Q denotes an R6 and R7 bridging substituted or unsubstituted group having 1 to 10 carbon atoms.

In a further preferred embodiment of the invention, R6 and R7 in formula (II), independently of one another, denote a secondary or tertiary carbon atom. In a most particularly preferred embodiment of the invention, one of the two groups R6 and R7 denotes a secondary carbon atom, while the respective other group R6 or R7 denotes a tertiary carbon atom.

In a further preferred embodiment of the invention, Q denotes an R6 and R7 bridging substituted or unsubstituted group, wherein the portion of Q bridging R6 and R7 is selected so that a four-, five-, six-, seven- or eight-membered ring is present. Q is particularly preferred when the portion of Q bridging R6 and R7 is selected so that a five- or six-membered ring is present.

In a further preferred embodiment of the invention, the ketone of general formula (II) contains at least one semicyclic or exocyclic double bond. Storing a scent comprising at least one cyclic double bond via this cyclic double bond, wherein the scent comprises at least one additional semicyclic or exocyclic double bond, poses a particular challenge, since frequently it is not possible to achieve sufficient selectivity between the double bonds, or the scent is even selectively stored via the semicyclic or exocyclic double bond. These undesirable isomers are not cleaved at all, or at least not at a sufficient rate, upon irradiation with natural sunlight or a commercially available luminous element, so that the scent impression of a multi-component perfume oil mixture may be decisively changed. In contrast, the method according to the invention makes it possible to selectively store a scent comprising at least one cyclic double bond via the cyclic double bond of the same, regardless of the number and chemical properties of further semicyclic or exocyclic double bonds.

The bridging portion —CH—R7-Q-R6- of the ketone of general formula (II) is preferably a hydrocarbon, as was already described above.

In a most particularly preferred embodiment of the invention, the ketone of general formula (II) is dihydrocarvone.

The ketone of general formula (II) is used in relation to the phosphonate of general formula (III) at a ratio of preferably 1:20 to 20:1, more preferably 1:10 to 10:1, still more preferably 1:5 to 5:1, and most preferably 1:2 to 2:1.

The resulting alpha,beta-unsaturated ketone of general formula (V) is preferably purified by way of distillation, crystallization and/or chromatographic separation methods, which are known to the person skilled in the art.

The alpha,beta-unsaturated ketone of general formula (V) is preferably hydrogenated in the presence of a catalyst and an alkali metal borohydride and selectively results in a ketone of general formula (I). The catalyst is preferably palladium adsorbed on activated carbon, as is sufficiently known from the prior art. Sodium borohydride is a particularly preferred alkali metal borohydride.

Hydrogenation is preferably carried out in a solvent. Suitable solvents can, for example, be selected from the group consisting of alcohols, water, carboxylic acid esters, halogen alkanes, aromatic solvents or mixtures thereof, toluene being a particularly preferred solvent within the meaning of the present invention.

The hydrogenation of the alpha,beta-unsaturated ketone of general formula (V) is preferably carried out at room temperature, which is to say 20 to 25° C., and normal pressure, which is to say 0.9 to 1.1 bar. Optionally, however, it may be preferred to carry out the hydrogenation at lower or higher temperatures and/or in particular at a higher pressure.

A further subject matter of the invention is a ketone of general formula (VI), which is obtainable by reacting
 a) dihydrocarvone with a benzonitrile of general formula (IV) in the presence of a phosphonate of general formula (III), and
 b) subsequently selectively hydrogenating the alpha,beta-unsaturated ketone obtained in step a) to yield a ketone of general formula (VI).

Previously, it was not possible to selectively produce ketones of general formula (VI); however, they are of particular interest from a perfume-related point of view since the stored scent is limonene. Limonene is one of the most important base components for multi-component perfume oil mixtures and conveys a fresh scent impression to the consumer, which is associated with cleanliness.

A further subject matter of the invention is a product comprising at least one compound of general formula (I),

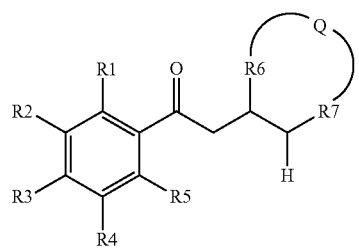

Formula (I)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, and R6 and R7, independently of one another, denote a secondary, tertiary or quaternary C-atom, and Q denotes an R6 and R7 bridging substituted or unsubstituted group having 1 to 10 carbon atoms, producible by a method in which a) a ketone of general formula (II)

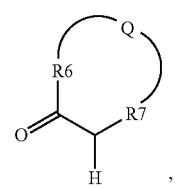

Formula (II)

where the groups R6, R7 and Q are identical to general formula (I), in the presence of a phosphonate of general formula (III),

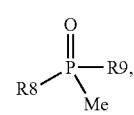

Formula (III)

where R8 and R9, independently of one another, each denote a linear or branched, substituted or unsubstituted alkoxy group having 1 to 15 carbon atoms, is reacted with a benzonitrile of general formula (IV),

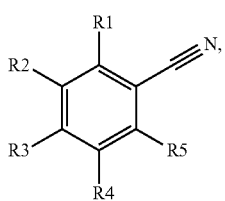

Formula (IV)

where the groups R1, R2, R3, R4 and R5 are identical to general formula (I), and subsequently
b) the alpha,beta-unsaturated ketone of general formula (V) obtained in step a),

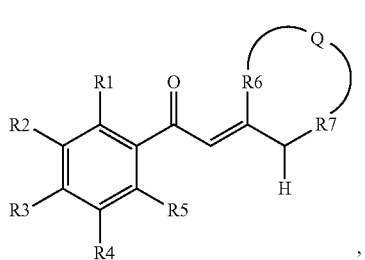

Formula (V)

where the groups R1 to R7 and Q are identical to general formula (I),
is selectively hydrogenated to yield a ketone of general formula (I).

In a preferred embodiment of the invention, the product is a detergent or cleaning agent, a cosmetic agent, an adhesive or a printing ink, detergents or cleaning agents and cosmetic agents being particularly preferred.

In a preferred embodiment of the invention, such a product contains the ketone of general formula (I) in quantities between 0.0001 and 10 wt. %, advantageously between 0.0005 and 5 wt. %, more advantageously between 0.001 and 3 wt. %, in particular between 0.005 and 2 wt. %, the respective percent by weight being based on the total product.

In a preferred embodiment of the invention, a product containing a ketone of general formula (I), such as a detergent or cleaning agent, a cosmetic agent, an adhesive or a printing ink, contains at least one further scent. The preferred used scents or perfume oils are not subject to any limitations whatsoever. For example, synthetic or natural scent compositions of the type esters, ethers, aldehydes (fragrant aldehydes), ketones (fragrant ketones), alcohols, hydrocarbons, acids, carbonate esters, aromatic hydrocarbons, aliphatic hydrocarbons, saturated and/or unsaturated hydrocarbons, and mixtures thereof can preferably be used as scents.

All customary fragrant aldehydes or fragrant ketones that are typically used to create a pleasant scent perception can be used as fragrant aldehydes or fragrant ketones. A person skilled in the art is generally familiar with suitable fragrant aldehydes and fragrant ketones. The fragrant ketones can include all ketones that are able to impart a desirable smell or a perception of freshness. It is also possible to use mixtures of different ketones. Ketones that may be used are, for example, alpha-damascone, delta-damascone, iso-damascone, carvone, gamma methyl ionone, Iso E Super, 2,4,4,7-tetramethyl-oct-6-en-3-one, benzylacetone, beta-damascone, damascenone, methyl dihydrojasmonate, methyl cedrylone, hedione, and mixtures thereof. Suitable fragrant aldehydes can be arbitrary aldehydes that convey a desired smell or a perception of freshness, corresponding to the fragrant ketones. These may, in turn, be individual aldehydes or aldehyde mixtures. Suitable aldehydes are melonal, triplal, ligustral, adoxal, lilial and the like, for example. The fragrant aldehydes and fragrant ketones can have an aliphatic, cycloaliphatic, aromatic, ethylenically unsaturated structure, or a combination of these structures. Moreover, further heteroatoms or polycyclic structures may be present. The structures can comprise suitable substituent, such as hydroxyl or amino groups. For example, suitable scents of the ester type are benzyl acetate, phenoxyethyl isobutyrate, p-tert butylcyclohexyl acetate, and so forth. Scent compounds of the hydrocarbon type are terpenes, for example, such as limonene and pinene. Suitable scents of the ether type are benzyl ethyl ether and Ambroxan, for example. Suitable fragrant alcohols are, for example, 10-undecen-1-ol, 2,6-dimethylheptan-2-ol, 2-methylbutanol, 2-methylpentanol, 2-phenoxyethanol, 2-phenylpropanol, and so forth. Scents or perfume oils can also be natural scent mixtures, such as those accessible from plant sources. The scents or perfume oils can also be essential oils, such as angelica oil, anise oil, arnica flower oil, and so forth. The total quantity of the at least one further scent in the product, such as a detergent or cleaning agent, a cosmetic agent, an adhesive or a printing ink, is preferably between 0.001 and 5 wt. %, advantageously between 0.01 and 4 wt. %, more advantageously between 0.1 and 3 wt. %, and most particularly preferably between 0.5 and 2 wt. %, based on the total product. Preferably, mixtures of different scents from the different above-mentioned scent classes are used, which together produce an appealing odorous note.

In a preferred embodiment of the invention, the products, such as detergents or cleaning agents, cosmetic agents, adhesives or printing inks, contain at least one surfactant, preferably selected from the group consisting of anionic, cationic, nonionic, zwitterionic, amphoteric surfactants or the mixtures thereof.

A preferred product can be solid or liquid, liquid products, in particular detergents or cleaning agents or additional laundry care products, being preferred. In particular if the product is a detergent or a cleaning agent, it is preferred for the product to contain at least one surfactant selected from the group consisting of anionic, nonionic, zwitterionic and amphoteric surfactants. In particular if the product is a softening detergent ("2-in-1"), it is preferred for the product to contain a softening component and at least one surfactant selected from the group consisting of anionic, nonionic, zwitterionic and amphoteric surfactants. Additional laundry care products are used for the targeted pretreatment of the laundry prior to washing in the case of stains or heavy soiling. Additional laundry care products include pre-wash detergents, pre-soak detergents, color run removers, and stain removers.

In particular if the product is a fabric softener, it is preferred for the product to contain a softening component. Fabric softeners are preferred as products since they only come in contact with the textiles in the last step of a conventional textile washing process, this being the rinse cycle, and thus attach as large a quantity of the scent as possible to the textile, without the risk of the scents being removed again in subsequent steps. It is most particularly preferred for the softening component to be an alkylated quaternary ammonium compound, at least one alkyl chain being interrupted by an ester or amido group. For example, the softening component includes quaternary ammonium compounds, such as monoalk(en)yltrimethylammonium compounds, dialk(en)yldimethylammonium compounds, mono-, di- or triesters of fatty acids with alkanol amines. Further softening components that may be used are quaternized protein hydrolysates or protonated amines. Moreover, cationic polymers are also suitable softening components. Polyquaternized polymers (such as Luviquat® Care from BASF) and chitin-based cationic biopolymers and the derivatives thereof, such as the polymer available under the trade name of Chitosan® (manufacturer: Cognis), can likewise be used. Further suitable softening components comprise protonated or quaternized polyamines. Particularly preferred softening components are alkylated quaternary ammonium compounds, of which at least one alkyl chain is interrupted by an ester group and/or amido group. N-methyl-N-(2-hydroxy-ethyl)-N,N(ditalgacyloxyethyl)ammonium methosulfate or bis-(palmitoyloxyethyl)hydroxyethyl methylammonium methosulfate are most particularly preferred.

The product, in particular in the form of fabric softeners, can also contain nonionic softening components, such as in particular polyoxyalkylene glycerol alkanoates, polybutylenes, long-chain fatty acids, ethoxylated fatty acid ethanolamides, alkyl polyglucosides, in particular sorbitan mono-, di- and triesters, and fatty acid esters of polycarboxylic acids. The softening component is advantageously present in the fabric softener, as the product, in quantities from 0.1 to 80 wt. %, usually 1 to 40 wt. %, preferably 2 to 20 wt. %, and in particular 3 to 15 wt. %, and the at least one scent or the mixture of different scents is advantageously present in quantities of 0.1 to 20 wt. %, preferably 1 to 13 wt. %, and in particular 2 to 8 wt. %, in each case based on the total quantity of the product.

The product may optionally contain one or more nonionic surfactants as a further component, wherein those that are usually used in detergents can be used.

It is furthermore preferred for the product, in particular in the form of a detergent or cleaning agent, to additionally contain further advantageous ingredients, which are known to a person skilled in the art. For example, the product, in particular the detergent or cleaning agent, can contain further ingredients that further improve the application-related and/or aesthetic properties of the product, in addition to the surfactants and/or softening compounds. Within the scope of the present invention, preferred products additionally contain one or more substances from the group of builders, bleaching agents, bleach activators, enzymes, electrolytes, non-aqueous solvents, pH-setting agents, pro-fragrances, fluorescent agents, dyes, hydrotopics, foam inhibitors, silicone oils, anti-redeposition agents, optional brighteners, graying inhibitors, shrinkage preventers, anti-wrinkle agents, color transfer inhibitors, antimicrobial active agents, germicides, fungicides, antioxidants, preservatives, corrosion inhibitors, antistatic agents, bittering agents, ironing aids, repellents and impregnating agents, swelling and anti-slip agents, neutral filler salts and UV absorbers. In particular silicates, aluminum silicates, such as in particular zeolites, carbonates, salts of organic di- and polycarboxylic acids, and mixtures of these substances, shall be mentioned as builders that can be present in the products.

The product can be used as a cleaning agent, for example to clean hard surfaces. It may be a dishwashing agent, for example, which is used to clean dishes manually or in an automatic dishwasher. It can also be customary industrial or household cleaners, which are used to clean hard surfaces, such as furniture surfaces, tiles, wall and floor coverings. In addition to dishes, possible hard surfaces can also be all remaining hard surfaces, in particular made of glass, ceramics, plastic, wood or metal, in households and industry. As with all other products, these may be solid or liquid formulations, wherein solid formulations can be present as a powder, granules, extrudate, in pellet form, as a tablet, or as a pressed and/or molten shaped body. Liquid formulations can be solutions, emulsions, dispersions, suspensions, microemulsions, gels or pastes.

The production of solid products, which is to say detergents or cleaning agents, does not pose any difficulties and can in principle take place in the known manner, such as by way of spray drying or granulation, wherein optional peroxygen compounds and an optional bleach catalyst can be added later, if necessary. To produce products having increased bulk density, in particular in the range from 650 g/L to 950 g/L, a method comprising an extrusion step is preferred. The production of liquid products likewise does not pose any difficulties and can likewise be carried out in the known manner. The incorporation of the pro-fragrances can in particular be carried out together with other scents.

A further subject matter of the invention is the use of a ketone of general formula (I), producible by the method according to the invention, in a detergent or cleaning agent, a cosmetic agent, an adhesive or a printing ink, for prolonging the scent impression of the detergent or cleaning agent, cosmetic agent, adhesive or printing ink. Using the ketone of general formula (I) in an above-described product effectively masks a potentially unpleasant odor of other ingredients of an above-described product over an extended period.

Still another subject matter of the invention is the use of a ketone of general formula (I), producible by the method according to the invention, for prolonging the scent impression of a surface treated with a detergent or cleaning agent, a cosmetic agent, an adhesive or a printing ink. A ketone of general formula (I) generates an extended scent impression on a hard or soft surface treated with the ketone, which is perceived as pleasant and fresh by the consumer and is associated with cleanliness and purity, in particular in detergents or cleaning agents.

EXAMPLES

Production of Diethyl Methylphosphonate

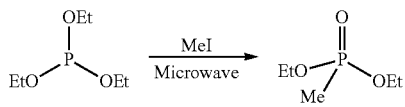

17.4 mL (100 mmol, 1 eq) triethyl phosphite and 11.3 mL (180 mmol, 1.8 eq) iodomethane were placed in a microwave vial and the same was sealed. Within 5 min, the mixture was heated to 120° C. at a power of 50 W, and this temperature was maintained for another 5 min. Subsequently, excess iodomethane and iodoethane that had developed were removed at 40° C. under high vacuum, whereby 14.9 g (98%) diethyl methylphosphonate was obtained.

$M(C_5H_{13}O_3P)$=152.13 g/mol $^1$H-NMR (CDCl$_3$, 500 MHz): δ [ppm]=3.65-3.53 (m, 4× H from CH$_2$), 0.97 (d, J=17.5 Hz, 3× H from CH$_3$ on P), 0.83 (t, J=7.2 Hz, 3× H from Et).

$^{13}$C-NMR (CDCl$_3$, 125 MHz): δ [ppm]=60.3 (2×CH$_2$), 15.4 (2×CH$_3$), 10.1 (1×CH$_3$).

$^{31}$P-NMR (CDCl$_3$, 200 MHz): δ [ppm]=31.2 (1× P).

MS (EtOAc, EI): m/z [%]=152 [M+] (4%), 137 (9%), 125 (86%), 123 (13%), 109 (9%), 108 (24%), 107 (24%), 97 (100%), 93 (6%), 91 (6%), 81 (18%), 80 (35%), 79 (89%), 65 (14%).

Production of 1-Benzoylmethylene Menthene

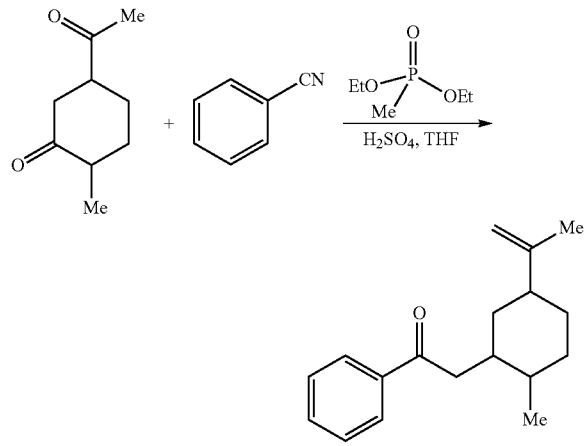

3.9 mL (26.3 mmol, 1 eq) diethyl methylphosphonate was dissolved in 130 mL THF, the solution was cooled to −78° C., 20.0 mL (31.6 mmol, 1.2 eq) n-BuLi (c=1.6 mol/L) was added dropwise, and the mixture was stirred for 90 min. Then 3.0 mL (28.9 mmol, 1.1 eq) benzonitrile was added dropwise and the mixture was allowed to thaw to −15° C. within 90 min. Then 2.2 mL (13.2 mmol, 0.5 eq) dihydrocarvone was added dropwise, the mixture was stirred for another 30 min at −15° C. and then stirred overnight at room temperature. Finally, 10 ml sulfuric acid (c=2.5 mol/L) was added, stirred for another 60 min, 30 mL water was added, the phases were separated, the aqueous phase was extracted twice with 50 mL diethyl ether, the united organic phases were washed with 50 mL saturated sodium chloride solution, and dried over magnesium sulfate. The solvent was removed under vacuum, whereby the raw product was obtained in the form of a mixture of diastereomers.

$M(C_{18}H_{22}O)=254.37$ g/mol

MS (EtOAc, EI): m/z [%]=254 [M+] (57%), 211 (47%), 197 (9%), 178 (10%), 165 (11%), 149 (12%), 134 (11%), 128 (11%), 119 (25%), 115 (17%), 107 (20%), 106 (16%), 105 (100%), 94 (13%), 93 (18%), 91 (32%), 79 (16%), 78 (17%), 77 (45%), 51 (10%).

Production of 3-Phenacyl Menthene

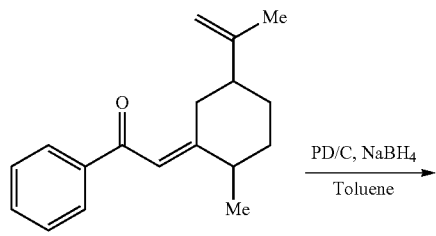

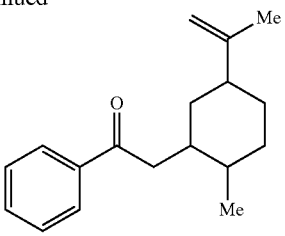

1.0 g (3.9 mmol, 1 eq) 1-benzoyl methylene menthene was dissolved in 15 mL toluene, 0.5 mL (7.9 mmol, 2 eq) acetic acid and 106 mg (98.3 μmol, 0.025 eq) Pd/C (10%) were added, and finally 0.6 g (15.7 mmol, 4 eq) sodium borohydride was added. The mixture was stirred for one hour, then excess sodium borohydride was deactivated with hydrochloric acid (c=0.1 mol/L), neutralized with saturated sodium hydrogen carbonate solution, the catalyst was filtered off by way of a fine mesh filter, the phases were separated, the aqueous phase was extracted twice with 50 mL diethyl ether, the united organic phases were washed with 50 mL water, and dried over magnesium sulfate. The solvent was removed under vacuum, whereby 756 mg raw product of 3-phenacyl menthene was obtained.

$M(C_{18}H_{24}O)=256.38$ g/mol

MS (EtOAc, EI): m/z [%]=256 [M+] (8%), 238 (12%), 213 (10%), 207 (13%), 181 (10%), 170 (13%), 145 (12%), 136 (34%), 128 (11%), 121 (55%), 120 (85%), 119 (24%), 107 (22%), 105 (100%), 95 (15%), 94 (37%), 93 (42%), 92 (16%), 91 (35%), 81 (18%), 79 (30%), 78 (25%), 77 (70%), 67 (22%), 51 (16%).

Exposure of 3-Phenacyl Menthene to Light

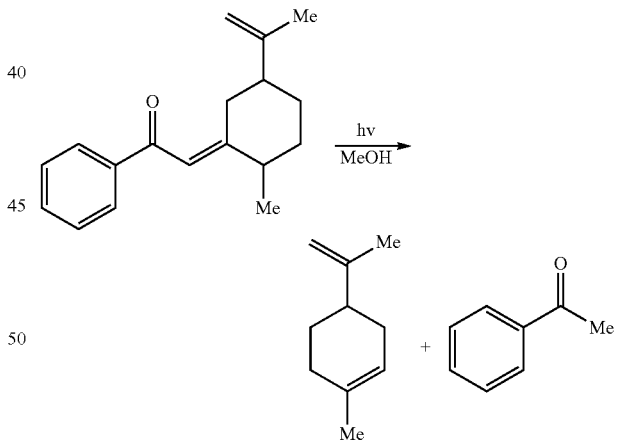

110 mg 3-phenacyl menthene was dissolved in 10 mL methanol (c=4×10⁻² mol/L) and exposed to light at lambda$_{max}$=300 nm for 18 h. The reaction was tracked by way of gas chromatography. After 18 h, the 3-phenyl menthene was substantially cleaved, and new signals were detected by way of NMR, which are assigned to limonene and acetophenone.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for producing a ketone of general formula (I),

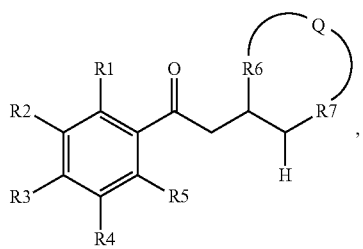

Formula (I)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —NH$_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, and R6 and R7, independently of one another, denote a secondary, tertiary or quaternary C-atom, and Q denotes an R6 and R7 bridging substituted or unsubstituted group having 1 to 10 carbon atoms, characterized in that a) a ketone of general formula (II)

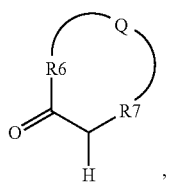

Formula (II)

where the groups R6, R7 and Q are identical to general formula (I),
in the presence of a phosphonate of general formula (III),

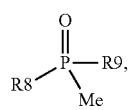

Formula (III)

where R8 and R9, independently of one another, each denote a linear or branched, substituted or unsubstituted alkoxy group having 1 to 15 carbon atoms, is reacted with a benzonitrile of general formula (IV),

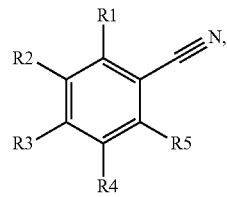

Formula (IV)

where the groups R1, R2, R3, R4 and R5 are identical to general formula (I), and subsequently b) the alpha,beta-unsaturated ketone of general formula (V) obtained in step a),

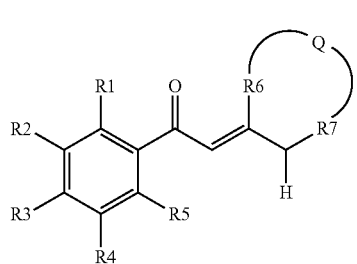

Formula (V)

where the groups R1 to R7 and Q are identical to general formula (I), is selectively hydrogenated to yield a ketone of general formula (I).

2. The method according to claim 1, characterized in that the ketone of general formula (II) comprises at least one semicyclic or exocyclic double bond.

3. The method according to claim 1, characterized in that the bridging portion —CH—R7-QR-6- of the ketone of general formula (II) is a hydrocarbon.

4. The method according to claim 1, characterized in that the ketone of general formula (II) is dihydrocarvone.

5. The method according to claim 1, characterized in that the groups R8 and R9 of the phosphonate of general formula (III), independently of one another, are each methoxy, ethoxy, propoxy, butoxy or isopropoxy residues.

6. The method according to claim 1, characterized in that the groups R1 to R5, independently of one another, each denote hydrogen, methyl groups or methoxy groups.

7. The method according to claim 1, characterized in that the hydrogenating agent is selected from the group of alkali metal borohydrides.

8. A ketone of general formula (VI)

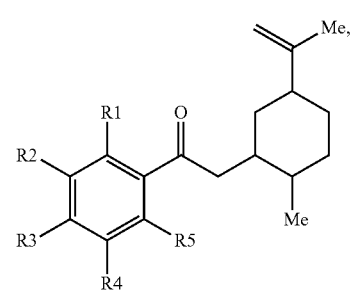

Formula (VI)

where R1, R2, R3, R4 and R5, independently of one another, can each denote hydrogen, —NO$_2$, a linear or branched, substituted or unsubstituted alkoxy group having 1 to 15 carbon atoms, a linear or branched, substituted or unsubstituted alkyl group having 1 to 15 carbon atoms, a cycloalkyl, acyl, aryl or heteroaryl group having 1 to 15 carbon atoms, —OH, —$NH_2$, halogen, —NH-alkyl, —N(alkyl)$_2$ or —N$^+$(alkyl)$_3$, or R1 and R2, or R2 and R3, can denote a bridging substituted or unsubstituted cycloalkyl, cycloalkenyl, aryl or heterocycle residue, producible by a) reacting dihydrocarvone with a benzonitrile of general formula (IV)

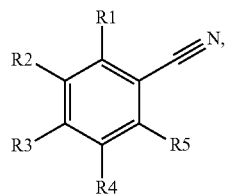

Formula (IV)

where the groups R1, R2, R3, R4 and R5 are identical to general formula (VI), in the presence of a phosphonate of general formula (III),

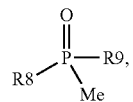

Formula (III)

where R8 and R9, independently of one another, each denote a linear or branched, substituted or unsubstituted alkoxy group having 1 to 15 carbon atoms, and subsequently b) selectively hydrogenating the alpha,beta-unsaturated ketone obtained in step a) to yield a ketone of general formula (VI).

* * * * *